(12) United States Patent
Plumptre

(10) Patent No.: US 10,668,218 B2
(45) Date of Patent: Jun. 2, 2020

(54) HOUSING AND CAP FOR AN INJECTION DEVICE MADE OF AN OUTER METAL PART AND AN INNER PLASTIC PART

(71) Applicant: Sanofi-Aventis Deutschland GMBH, Frankfurt am Main (DE)

(72) Inventor: David Aubrey Plumptre, Worcestershire (GB)

(73) Assignee: Sanofi-Aventis Deutschland GMBH, Frankfut am Main (DE)

( * ) Notice: Subject to any disclaimer, the term of this patent is extended or adjusted under 35 U.S.C. 154(b) by 151 days.

(21) Appl. No.: 14/914,472

(22) PCT Filed: Aug. 26, 2014

(86) PCT No.: PCT/EP2014/068023
§ 371 (c)(1),
(2) Date: Feb. 25, 2016

(87) PCT Pub. No.: WO2015/028441
PCT Pub. Date: Mar. 5, 2015

(65) Prior Publication Data
US 2016/0206820 A1    Jul. 21, 2016

(30) Foreign Application Priority Data
Aug. 29, 2013  (EP) ..................... 13182221

(51) Int. Cl.
*A61M 5/31* (2006.01)
*A61M 5/32* (2006.01)
(Continued)

(52) U.S. Cl.
CPC ............ *A61M 5/3129* (2013.01); *A61M 5/31* (2013.01); *A61M 5/31536* (2013.01);
(Continued)

(58) Field of Classification Search
CPC .............. A61M 5/3202; A61M 5/3213; A61M 2005/3201; A61M 5/3129; A61M 5/31;
(Continued)

(56) References Cited

U.S. PATENT DOCUMENTS 533,575 A    2/1895  Wilkens
4,865,591 A   9/1989  Sams
(Continued)

FOREIGN PATENT DOCUMENTS

CA    2138528    2/1994
CA    2359375    7/2000
(Continued)

OTHER PUBLICATIONS

Lug meaning—01182018 from Engineering Dictionary.*
(Continued)

*Primary Examiner* — Nathan R Price
*Assistant Examiner* — Dung T Ulsh
(74) *Attorney, Agent, or Firm* — Fish & Richardson P.C.

(57) ABSTRACT

A housing and a cap for a drug delivery device is provided, comprising a metal element (150, 132) and a plastic element (131, 133) which together form a functional unit. The metal element (150, 132) and the plastic element (131, 133) are fixedly coupled to each other, and the metal element (150, 132) provides an outer surface of the assembly which is configured to be handled by a user. Furthermore, a drug delivery device (1) is provided comprising the housing or cap, and having a weight less than 30 g. Furthermore, a method of producing a housing or a cap is provided, wherein the metal element (150, 132) is slid over the plastic element (131, 133) in a longitudinal direction.

20 Claims, 13 Drawing Sheets

(51) Int. Cl.
*A61M 5/315* (2006.01)
*A61M 5/24* (2006.01)

(52) U.S. Cl.
CPC ....... *A61M 5/3202* (2013.01); *A61M 5/31551* (2013.01); *A61M 5/31585* (2013.01); *A61M 2005/2407* (2013.01); *A61M 2005/2488* (2013.01); *A61M 2005/3104* (2013.01); *A61M 2005/3154* (2013.01); *A61M 2207/00* (2013.01)

(58) Field of Classification Search
CPC .......... A61M 5/31536; A61M 5/31551; A61M 5/31585
See application file for complete search history.

(56) References Cited

U.S. PATENT DOCUMENTS

| | | | |
|---|---|---|---|
| 5,092,842 A * | 3/1992 | Bechtold | A61M 5/20 604/135 |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber | |
| 5,383,865 A | 1/1995 | Michel | |
| 5,391,157 A | 2/1995 | Harris | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman | |
| 5,851,079 A | 12/1998 | Horstman | |
| 5,921,966 A | 7/1999 | Bendek et al. | |
| 5,957,896 A | 9/1999 | Bendek | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 * | 4/2001 | Burroughs | A61M 5/31551 604/153 |
| 6,235,004 B1 | 5/2001 | Steenfeldt-Jensen et al. | |
| 6,248,095 B1 | 6/2001 | Giambattista et al. | |
| 6,432,087 B1 | 8/2002 | Hoeck et al. | |
| 6,562,006 B1 | 5/2003 | Hjertman | |
| 6,610,042 B2 | 8/2003 | Leon et al. | |
| 6,613,023 B2 | 9/2003 | Kirchhofer | |
| 6,699,224 B2 | 3/2004 | Kirchhofer | |
| 6,932,794 B2 | 8/2005 | Giambattista | |
| 6,936,032 B1 | 8/2005 | Bush, Jr. et al. | |
| 7,169,132 B2 | 1/2007 | Bendek | |
| 7,241,278 B2 | 7/2007 | Moller | |
| 7,678,084 B2 | 3/2010 | Judson | |
| 8,187,233 B2 | 5/2012 | Harms et al. | |
| 2002/0052578 A1 | 5/2002 | Moller | |
| 2002/0120235 A1 | 8/2002 | Enggaard | |
| 2003/0050609 A1 | 3/2003 | Sams | |
| 2004/0015038 A1 | 1/2004 | Piere-Marie | |
| 2004/0059299 A1 | 3/2004 | Moller | |
| 2004/0097883 A1 | 5/2004 | Roe | |
| 2004/0162517 A1 * | 8/2004 | Furst | A61M 5/2046 604/69 |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0079847 A1 * | 4/2006 | Crawford | A61M 25/0631 604/192 |
| 2006/0153693 A1 | 7/2006 | Fiechter et al. | |
| 2006/0264827 A1 | 11/2006 | Whang | |
| 2007/0016143 A1 | 1/2007 | Miller et al. | |
| 2007/0265579 A1 | 11/2007 | Gennady et al. | |
| 2009/0069753 A1 * | 3/2009 | Ruan | A61M 5/3202 604/192 |
| 2009/0108007 A1 * | 4/2009 | Anderson | A61L 2/04 220/607 |
| 2009/0275916 A1 * | 11/2009 | Harms | A61M 5/24 604/506 |
| 2010/0106098 A1 | 4/2010 | Atterbury et al. | |
| 2010/0152667 A1 * | 6/2010 | Kietzmann | A61M 5/31556 604/189 |
| 2011/0054414 A1 * | 3/2011 | Shang | A61M 5/2033 604/218 |
| 2012/0153534 A1 * | 6/2012 | Etter | A61M 5/14244 264/254 |
| 2012/0197207 A1 * | 8/2012 | Stefanski | A61M 5/20 604/189 |
| 2012/0225405 A1 * | 9/2012 | Boehm | A61M 5/31513 433/90 |
| 2013/0060196 A1 * | 3/2013 | O'Connor | A61M 5/14566 604/152 |
| 2013/0204227 A1 * | 8/2013 | Bochenko | G06F 19/3456 604/506 |
| 2013/0261596 A1 * | 10/2013 | McKay | A61M 37/0069 604/506 |
| 2013/0265846 A1 * | 10/2013 | Bublewitz | A61M 5/31596 366/177.1 |
| 2014/0025013 A1 * | 1/2014 | Dowds | A61M 5/3129 604/198 |
| 2014/0046259 A1 * | 2/2014 | Reber | A61M 5/2033 604/136 |
| 2014/0162517 A1 | 6/2014 | Joly et al. | |
| 2014/0343503 A1 * | 11/2014 | Holmqvist | A61M 5/3202 604/192 |
| 2015/0174325 A1 * | 6/2015 | Young | A61M 5/2033 604/135 |
| 2015/0174337 A1 * | 6/2015 | Takemoto | A61M 5/3202 604/192 |
| 2016/0067413 A1 * | 3/2016 | Madin | A61M 5/3202 604/222 |
| 2016/0106929 A1 * | 4/2016 | Fournier | A61M 5/3202 604/192 |
| 2016/0144132 A1 * | 5/2016 | Scanlon | A61M 5/3202 604/192 |
| 2016/0151577 A1 * | 6/2016 | Newton | A61M 5/31551 604/224 |
| 2016/0193414 A1 * | 7/2016 | McLoughlin | A61M 5/24 604/192 |
| 2016/0213857 A1 * | 7/2016 | Plumptre | A61M 5/3202 |
| 2016/0271336 A1 * | 9/2016 | Thomsen | A61M 5/3137 |

FOREIGN PATENT DOCUMENTS

| | | |
|---|---|---|
| CN | 1780652 | 5/2006 |
| CN | 201097144 | 8/2008 |
| CN | 101663060 | 3/2010 |
| CN | 102470214 | 5/2012 |
| DE | 1561832 | 4/1970 |
| EP | 0496141 | 7/1992 |
| EP | 0897729 | 2/1999 |
| EP | 0937471 | 8/1999 |
| EP | 0937476 | 8/1999 |
| EP | 1603611 | 12/2005 |
| EP | 1776975 | 4/2007 |
| GB | 0304822.0 | 3/2003 |
| GB | 0304823.8 | 11/2017 |
| JP | H02-502971 | 1/1994 |
| JP | 2001-063283 | 3/2001 |
| JP | 2002-052081 | 2/2002 |
| JP | 2006-519074 | 8/2006 |
| JP | 2006-305302 | 11/2006 |
| JP | 2013-523294 | 6/2013 |
| WO | WO88/08725 | 11/1988 |
| WO | WO 93/07922 | 4/1993 |
| WO | WO 93/24160 | 12/1993 |
| WO | WO 1999/038554 | 8/1999 |
| WO | WO 2001/010484 | 2/2001 |
| WO | WO 02/030495 | 4/2002 |
| WO | WO 02/092153 | 11/2002 |

(56) References Cited

FOREIGN PATENT DOCUMENTS

| WO | WO 03/080160 | 10/2003 |
| WO | WO 2004/078239 | 9/2004 |
| WO | WO 2006/084876 | 8/2006 |
| WO | WO2008/128645 | 10/2008 |
| WO | WO 2010/089417 | 8/2010 |
| WO | WO 2010/112558 | 10/2010 |
| WO | WO 2011/124633 | 10/2011 |
| WO | WO2015/028441 | 3/2015 |

OTHER PUBLICATIONS

Definition of couple (Merriam-Webster Aug. 3, 2018).*
Definition of cap (Merriam-Webster Aug. 3, 2018).*
International Search Report and Written Opinion in International Application No. PCT/EP2014/068023, dated Feb. 9, 2015, 7 pages.
International Preliminary Report on Patentability in International Application No. PCT/EP2014/068023, dated Mar. 1, 2016, 13 pages.
Rote Liste, "50. Hypophysen-, Hypothalamushormone, andere regulatorische Peptide u. ihre Hemmstoffe," Chapter 50, ed. 2008, 20 pages.
"Pen-injectors for medical use—Part 1: Pen-injectors—Requirements and test methods," International Standard, reference number: ISO 11608-1:2000(E), first edition Dec. 15, 2000, 32 pages.

* cited by examiner

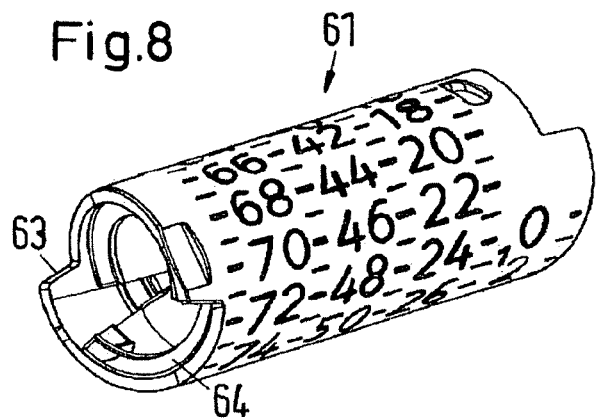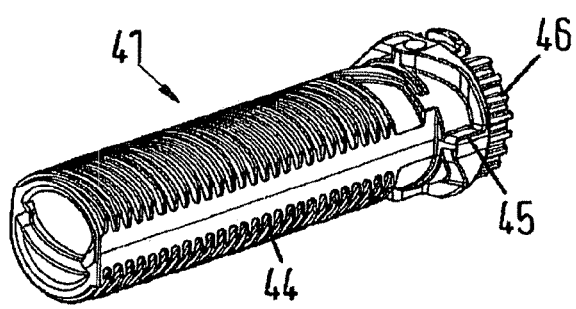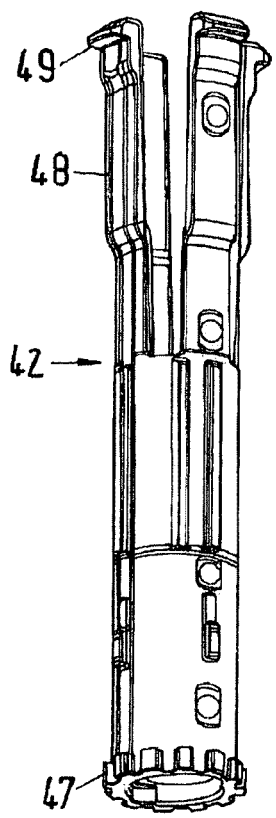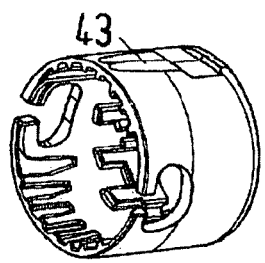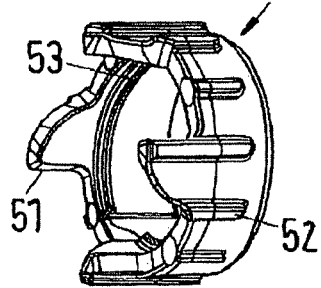

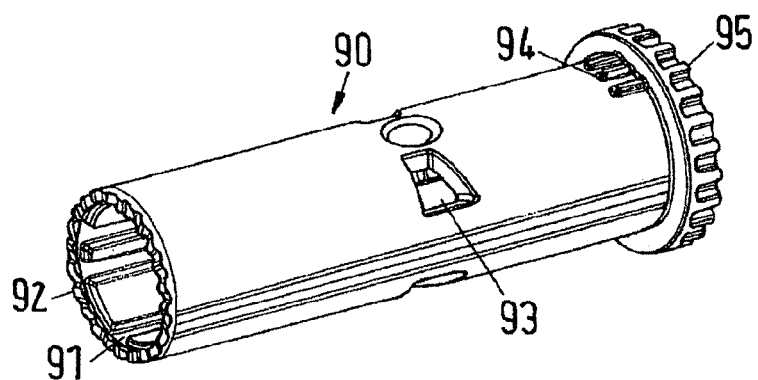
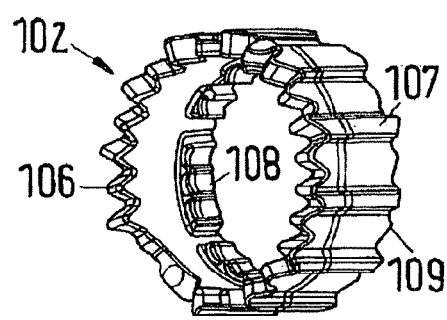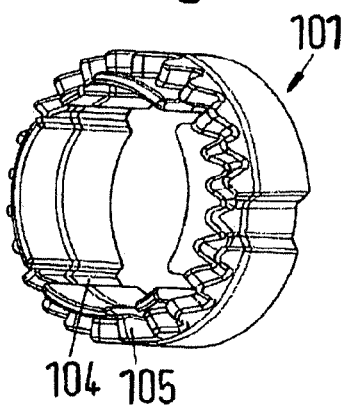
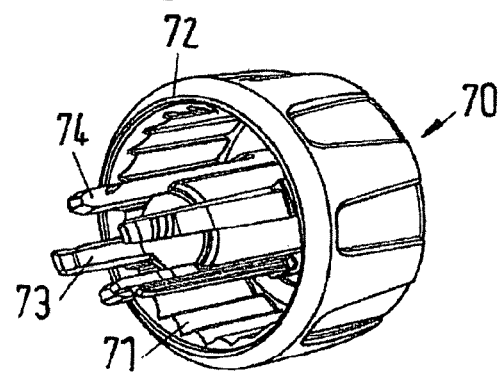

HOUSING AND CAP FOR AN INJECTION DEVICE MADE OF AN OUTER METAL PART AND AN INNER PLASTIC PART

CROSS-REFERENCE TO RELATED APPLICATIONS

This application is a U.S. national stage application under 35 USC § 371 of International Application No. PCT/EP2014/068023, filed on Aug. 26, 2014, which claims priority to European Patent Application No. 13182221.5, filed on Aug. 29, 2013, the entire contents of which are incorporated herein by reference.

The present disclosure relates to an assembly for a drug delivery device. Furthermore, the present disclosure relates to a drug delivery device comprising the assembly and to a method of producing the assembly.

Drug delivery devices, in particular pen-type drug delivery devices, have application where regular injection by persons without formal medical training occurs. This may be increasingly common among patients having diabetes where self-treatment enables such patients to conduct effective management of their disease. In practice, such a drug delivery device allows a user to dispense a number of user variable doses or fixed doses of a medicament.

Aspects of the invention may include an assembly for a drug delivery device having improved properties. In particular, aspects of the invention may include a drug delivery device with a sophisticated design.

An assembly for a drug delivery device is provided, the assembly comprising a metal element and a plastic element which together form a functional unit. The metal element provides an outer surface of the assembly. The outer surface is configured to be handled by a user, in particular a user of the drug delivery device. In particular, the outer surface may provide a supporting surface for a hand of a user during a use of the drug delivery device. The metal element and the plastic element are fixedly coupled to each other. In particular, the metal component and the plastic component are rotationally and axially fixed with respect to each other.

The advantage of an assembly wherein a metal component forms an outer surface is that a user associates a metal surface with high quality. In particular, a metal surface has pleasant haptical properties to a user. For example a metal surface may feel smooth and cool. Furthermore, a metal surface may look more precious than a plastic surface. Yet, due to the plastic element, the assembly may have less weight than an assembly which is completely produced of metal. Thereby, a drug delivery device comprising the assembly is easier to handle by a user. Furthermore, the material costs are kept low without losing functional properties. In particular, the plastic element may improve the stability of the metal element. Due to the plastic element, the metal element may withstand forces acting on the metal element during an assembly of the drug delivery device. With the plastic element supporting the metal element, the metal element may be dimensionally stable. Additionally, the plastic element may be moulded with features that attach to other existing inner plastic components. Furthermore, the plastic element and/or the metal element may comprise other features, such as one or more stop features, for example an '80 Units stop' feature, that is/are configured or required to prevent the user from setting a dose greater than a predetermined maximum dose. In particular, such a stop feature may be configured so as to provide a defined rotational and/or axial stop for a dialing member of a drug delivery device, such as a dial sleeve or whatsoever. In this way, e.g. an axial travel of such a dialing member which corresponds to a dialed dose of a medicament can be delimited such that dose dialing can be restricted to a predetermined maximum dose. For example, in an end position of a dial sleeve with respect to the assembly a stop feature on the dial sleeve may be engaged with said stop feature of the metal element or the plastic element of the assembly, thereby determining a maximum set dose.

For example, the assembly may form an outer housing part or a cap for a drug delivery device. According to a conceivable embodiment, both a housing part and a cap for a drug delivery device may be formed by a respective assembly. In particular, the assembly may be a part for a drug delivery device which is often touched by a user. In case that the plastic element is a housing part, the plastic element may be attached to an inner housing body. In particular, the inner housing body may comprise retention features that may engage with the plastic element.

A functional unit may be an assembly which once assembled acts as one part. The metal element and the plastic element may be permanently or releasably coupled.

According to one embodiment, the length of the metal element and the plastic element may be essentially equal. According to another embodiment, the length of the plastic element may be less than the length of the metal element. For example, the length of the plastic element may be between one fourth and one half of the length of the metal element. Thereby, the plastic element may be easier and cheaper to produce.

The metal element may comprise aluminium or another metal material. An outer surface of the metal element may be anodised. The anodising provides a high quality and hard wearing exterior surface to the metal element. Furthermore, it enables it to be given a variety of metallic colours. In a further embodiment, the metal element may be galvanised. Alternatively, the metal element may be surface treated by brushing. Furthermore, the metal element may be varnished with a clear coating material.

The metal element may essentially comprise the shape of a sleeve. A wall thickness of the metal element may be between 0.3 mm and 0.6 mm. Preferably, the wall thickness of the metal element may be 0.4 mm. Thereby, the metal element may comprise a sufficient stability while having a low weight.

The metal element may be manufactured by deep drawing. Thereby, the metal element may comprise an end face which is inclined with respect to a longitudinal axis of the metal element. For example, the end face may be inclined about 60° to 80° with respect to the longitudinal axis of the metal element.

For example, the plastic element may comprise Polyoxymethylen or another plastic material. The plastic element may be produced by mold flowing.

The shape of the plastic element and the metal element may be adapted to each other. In particular, an outer surface of the plastic element may be adapted to an inner surface of the metal element in a large part. This means that only a small part of the outer surface of the plastic element, for example a part which is necessary to align the plastic element and the metal element with respect to each other, is not in contact with an inner surface of the metal element.

According to one embodiment, the metal element comprises one or more radial lugs. The metal element and the plastic element may be held together by the radial lug of the metal extending towards the plastic element. In particular, the radial lug may engage the plastic element. Thereby, an axial and rotational position of the metal element and the plastic element with respect to each other may be maintained. In particular, the metal element may be connected to the plastic element by means of the radial lug. The lug features are preferably formed by punching. The metal element and the plastic element may be connected by reshaping the metal element.

According to one embodiment, the metal element comprises one or more additional lug features, which are configured to serve as a stop feature, for example as an '80 Units stop' feature, instead of the plastic element. The additional lug features may be folded into the metal element. Preferably, the additional lug features do not contact the plastic element.

According to one embodiment, the assembly comprises an aperture. In particular, the metal element and the plastic element may each comprise an aperture which are aligned with each other. The aperture in the metal element may be cut out by blanking. The aperture in the plastic element may be provided during the moulding process.

According to one embodiment, the radial lug of the metal element may be located at the aperture. In order to secure the metal element and the plastic element with respect to each other, the radial lug is folded into the aperture.

The aperture may be provided for receiving a further component. For example, the aperture may be configured to receive a clip element. Alternatively, the aperture may receive a window component. In the window component, an amount of a set dose may be indicated to a user.

According to one embodiment, the metal element and the plastic element may be secured with respect to each other by the further component being received in the aperture. For example, the further component may stick through the aperture of the metal element. Thereby, the metal element and the plastic element may be held in a fixed position. Furthermore, the further component may be clipped in the plastic element.

According to one embodiment, the metal element may comprise an aperture. The plastic element may be made from a transparent material. In this embodiment, the window component may be comprised by the plastic element. In particular, no further window component is necessary.

According to one embodiment, the plastic element may comprise a protrusion. The protrusion may be located at an axial end of the plastic element. The protrusion may extend in a radial outward direction. The metal element may extend over the plastic element until it abuts the protrusion. Thereby, an axial position of the metal element with respect to the plastic element may be defined. Furthermore, the protrusion of the plastic element may comprise a nose which extends in a longitudinal direction. The nose may be configured to engage with a corresponding recess of the metal element. Thereby, a rotational position of the metal element with respect to the plastic element may be defined.

According to one embodiment, the metal element and the plastic element may be secured with respect to each other by press fitting.

According to one aspect of the disclosure, a drug delivery device is provided. The drug delivery device may comprise an assembly as described above. The drug delivery device may comprise further elements, such as a drive assembly, a cartridge holder and a cartridge. The drug delivery device may have a weight of less than 30 g. For example, the drug delivery device may have a weight of less than 30 g containing a cartridge which is full with a medicament. Alternatively, the drug delivery device may have a weight of less than 30 g containing an empty cartridge. This may be achieved by the combination of a metal element and a plastic element in one functional unit. A drug delivery device having a weight of less than 30 g has the advantage that it is easy to handle by a user.

The drug delivery device may be an injection device. The drug delivery device may be a pen-type device. The drug delivery device may be a fixed dose device such that the amount of medication which is delivered during one dispense operation is predetermined. In particular, a user may not be enabled to vary the size of the dose.

Alternatively, the drug delivery device may be a variable dose device such that the amount of medication which is delivered during one dispense operation may be adjusted by a user. The drug delivery device may be configured for multiple dose applications. The medication may be delivered to a user by means of a needle. The device may be delivered to a user in a fully assembled condition ready for use. The drug delivery device may be a reusable device. Alternatively, the drug delivery device may be a disposable device. The term "disposable" means that the drug delivery device cannot be reused after an available amount of medication has been delivered from the drug delivery device. The drug delivery device may be configured to deliver a liquid medication. The medication may be, for example, insulin.

According to a further aspect of the disclosure, a method of producing an assembly for a drug delivery device is provided. The method comprises the providing of a metal element and a plastic element. The metal element and the plastic element may have the shape of a sleeve. During assembling, the metal element is slid over the plastic element. In particular, the metal element is slid over the plastic element in a longitudinal direction.

The term "medication", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while ρ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A non-limiting, exemplary embodiment of the disclosure will now be described with reference to the accompanying drawings, in which:

FIG. 5b shows a detail of the inner body of FIG. 5a;

FIG. 7b shows a detail of the first display member of FIG. 7a;

FIG. 8 shows a second display member component of the drug delivery device of FIG. 1;

FIG. 9 shows a first driver component of the drug delivery device of FIG. 1;

FIG. 10 shows a second driver component of the drug delivery device of FIG. 1;

FIG. 11 shows a third driver component of the drug delivery device of FIG. 1;

FIG. 12 shows the last dose nut of the drug delivery device of FIG. 1;

FIG. 13 shows a clutch component of the drug delivery device of FIG. 1;

FIG. 14 shows a first clicker component of the drug delivery device of FIG. 1;

FIG. 15 shows a second clicker component of the drug delivery device of FIG. 1;

FIG. 16 shows the button of the drug delivery device of FIG. 1;

Figure 21A:
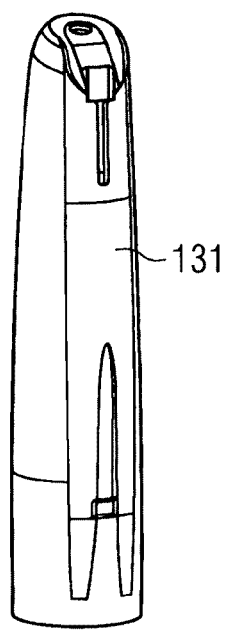
FIG. 21a shows a plastic element of a cap.
Figure 21B:
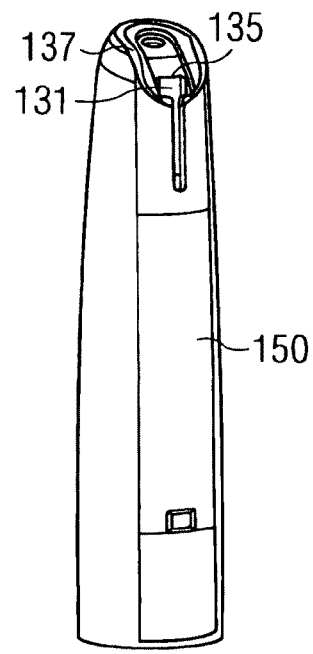
Figure 21C:
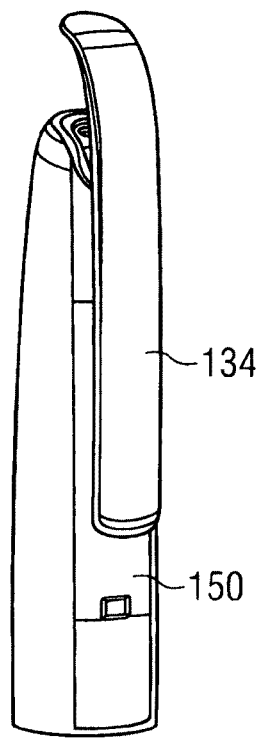
Figure 22A:
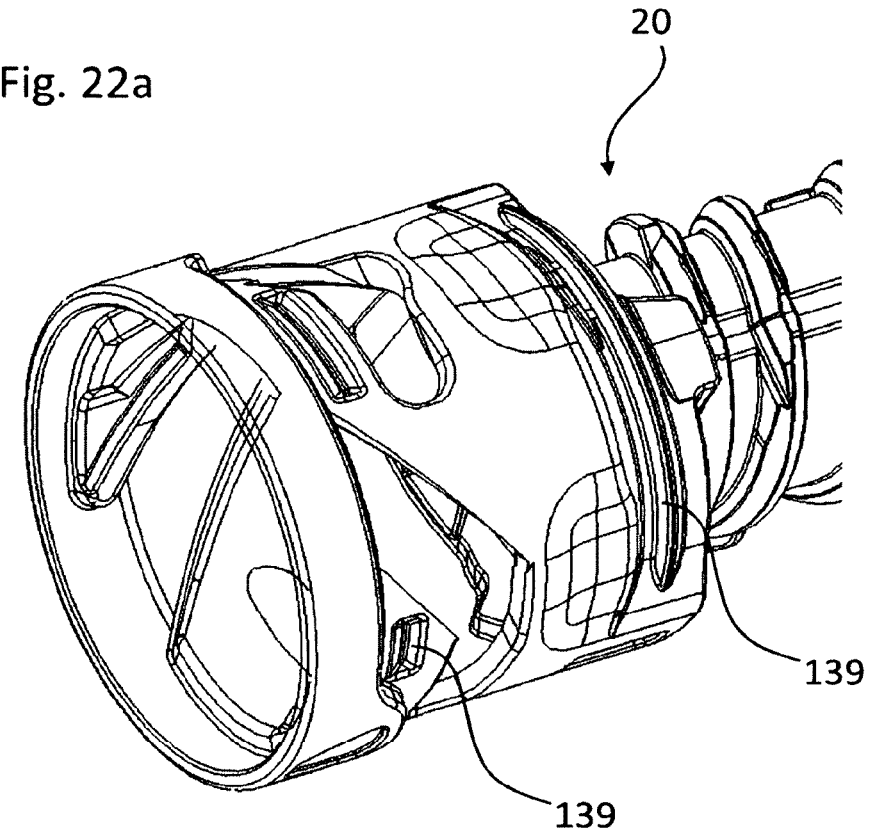
Figure 22B:
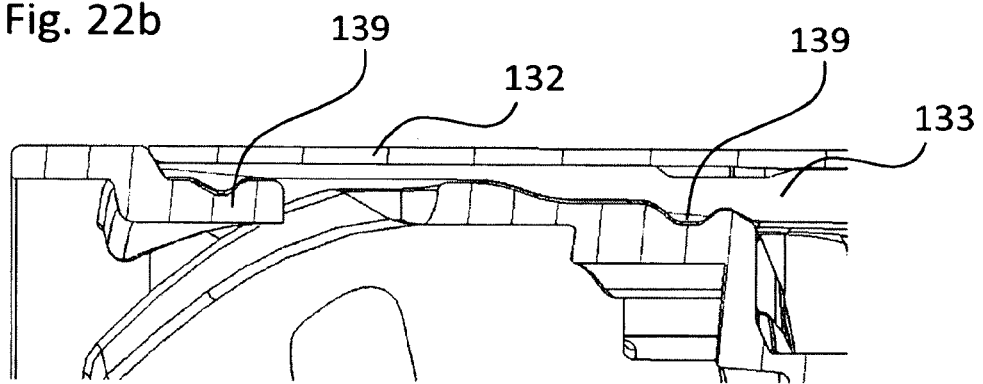
Figure 23A:
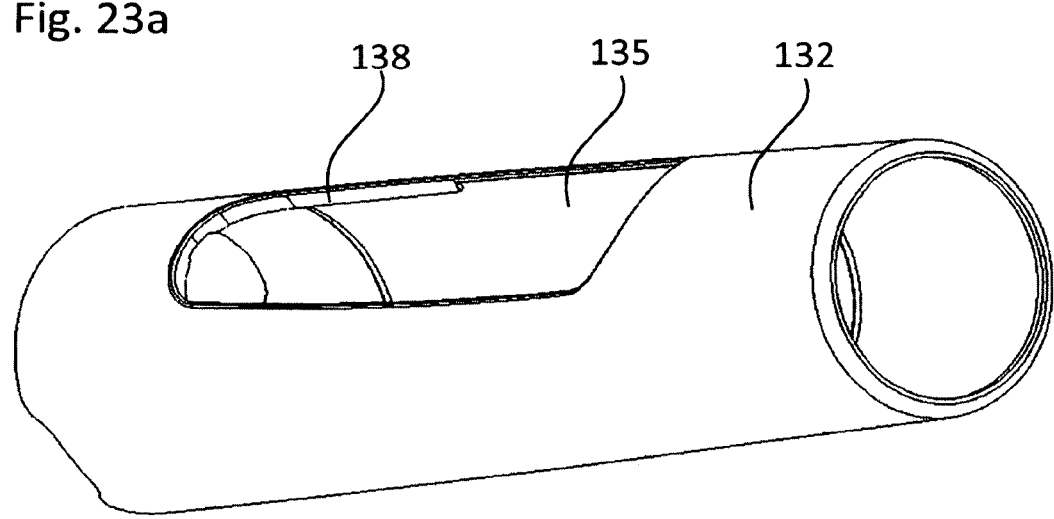
Figure 23B:
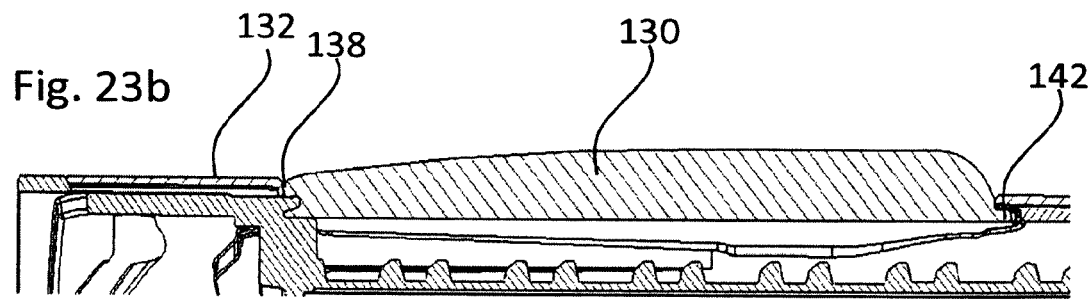
Figure 24A:
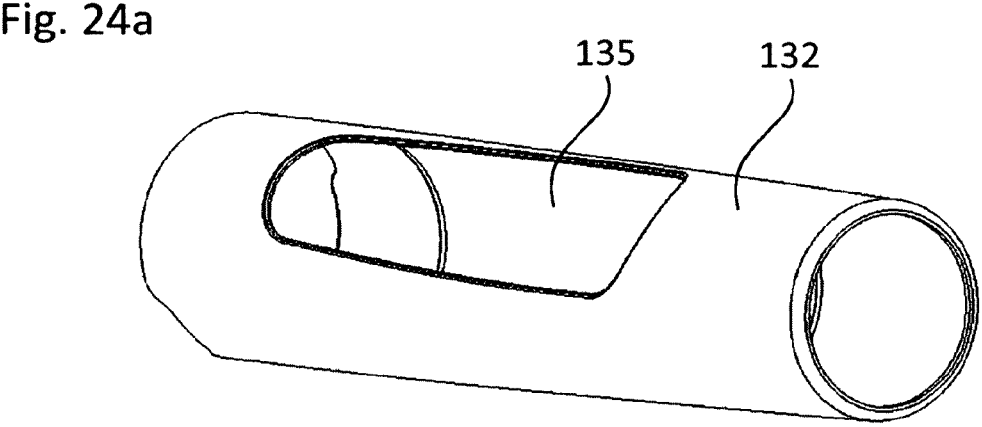
Figure 24B:
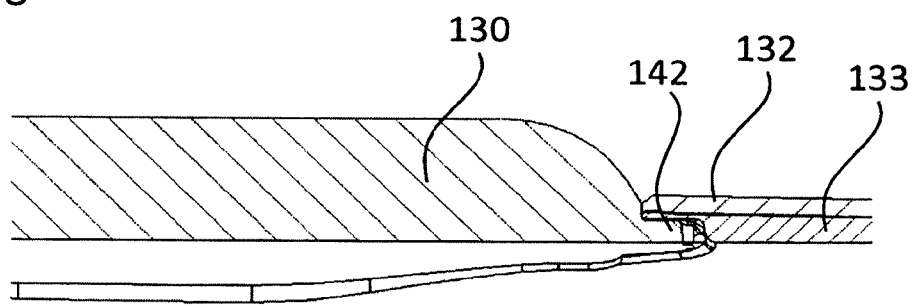
Figure 25A:
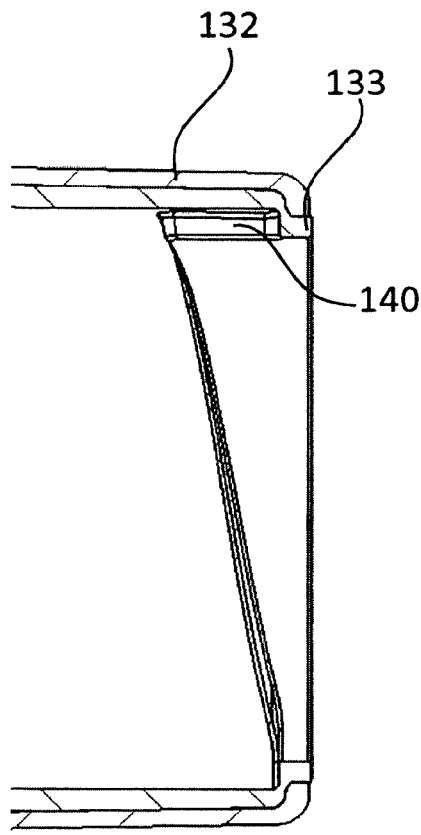
Figure 25B:
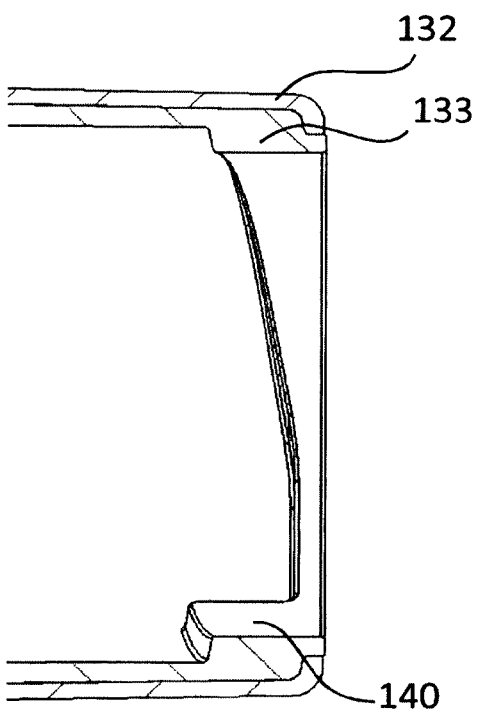
Figure 26:
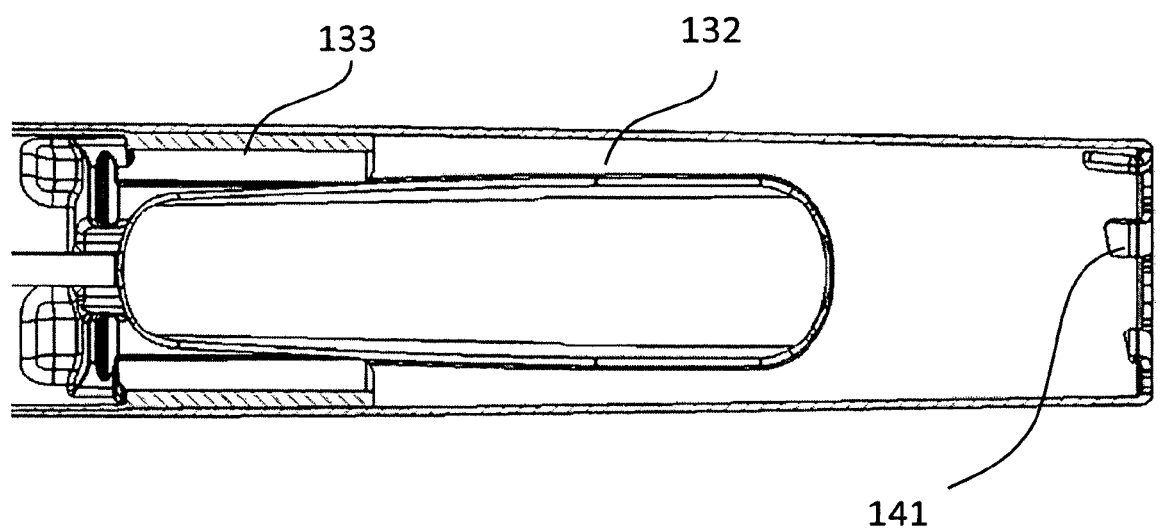
Figure 27:
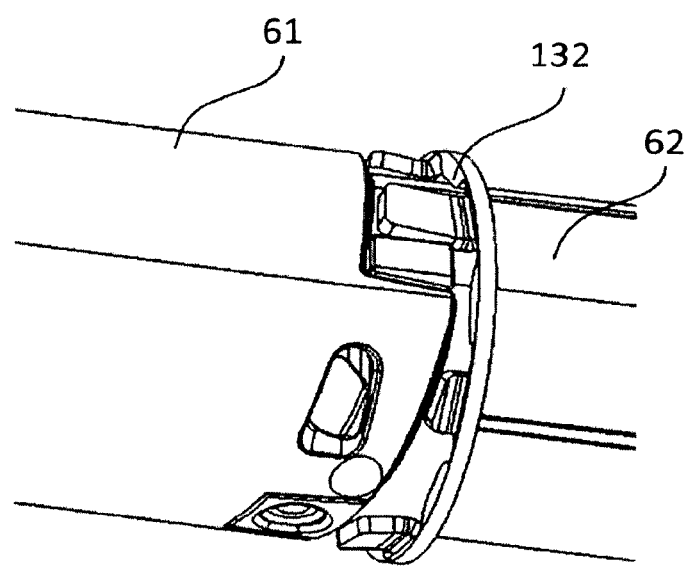

FIG. 21*b* shows the plastic element and a metal element of the cap;

FIG. 21*c* shows a clip element being attached to the cap;

FIG. 22*a* shows a snap feature of the inner housing;

FIG. 22*b* shows the outer housing part being coupled to the inner housing;

FIG. 23*a* shows a metal element of an outer housing part comprising a lug feature;

FIG. 23*b* shows an assembly comprising a metal element comprising a lug feature and a plastic element in a sectional view;

FIG. 24*a* shows a metal element of an outer housing part;

FIG. 24*b* shows an assembly comprising a metal element and a plastic element in a sectional view;

FIG. 25*a* shows a sectional view of a part of the outer housing part comprising a metal element and a plastic element;

FIG. 25*b* shows a further sectional view of the outer housing part of FIG. 25A;

FIG. 26 shows an '80 Units stop' feature which is arranged on the metal element of the outer housing part;

FIG. 27 shows an assembly comprising the metal element of FIG. 26.

Figure 1:
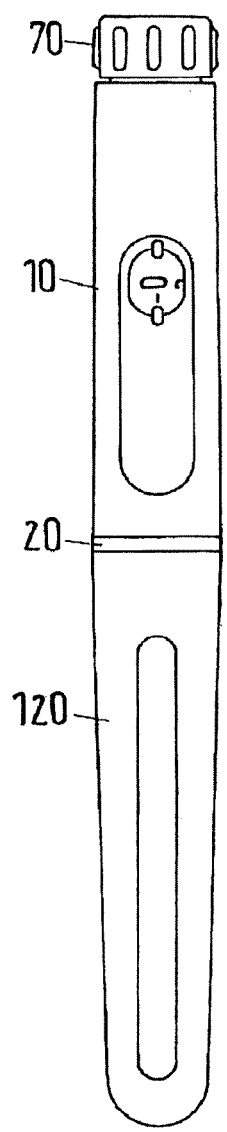
FIG. 1 shows a drug delivery device with a cap attached in accordance with the present disclosure.
Figure 2:
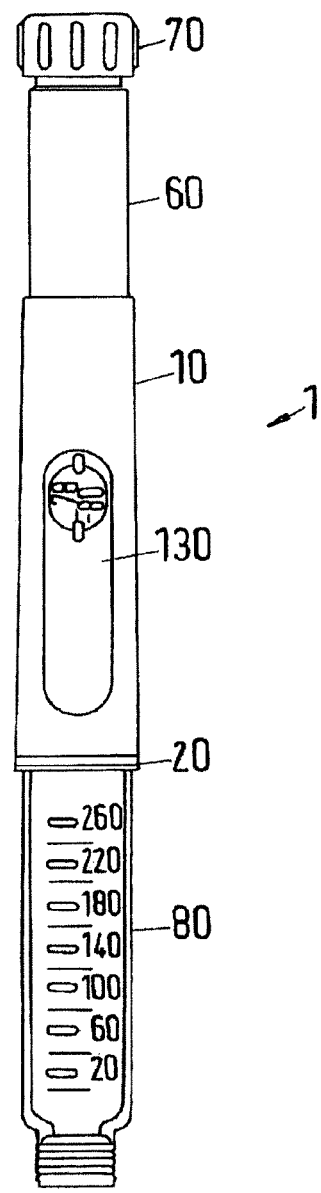
FIG. 2 shows the drug delivery device of FIG. 1 with the cap removed and a dose of 79 units dialed.
Figure 3:
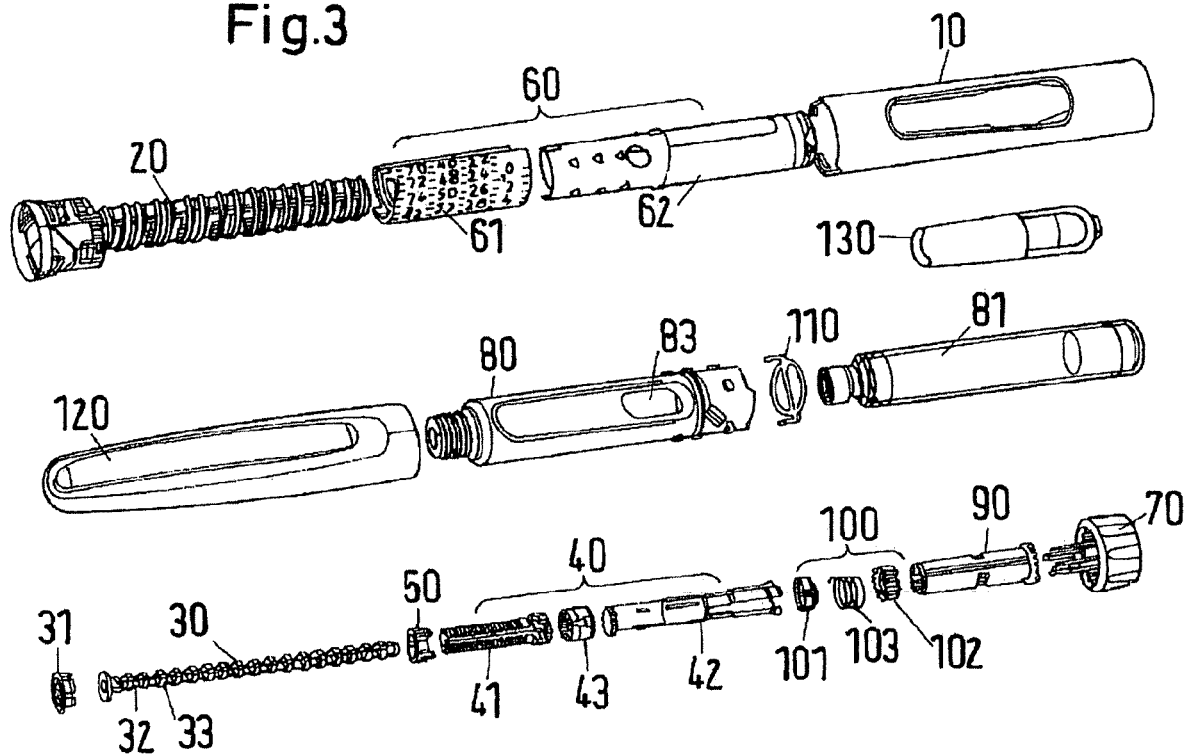
FIG. 3 shows in an exploded view the components of the drug delivery device of FIG. 1.

FIGS. 1 and 2 show a drug delivery device 1 in the form of an injection pen. The device has a distal end (lower end in FIG. 1) and a proximal end (upper end in FIG. 1). The component parts of the drug delivery device 1 are shown in FIG. 3 in more detail. The drug delivery device 1 comprises an outer housing part 10, an inner body 20, a piston rod 30, a driver 40, a nut 50, a display member 60, a button 70, a cartridge holder 80 for receiving a cartridge 81, a clutch 90, a clicker 100, a spring 110, a cap 120 and a window insert 130. A needle arrangement (not shown) comprising a needle hub and a needle cover may be provided as additional components, which can be exchanged as explained above. The piston rod 30 comprises a bearing 31. The driver comprises a distal driver part 41, a proximal driver part 42 and a coupler 43. The display member 60 comprises a number sleeve 61 and a dial sleeve 62. The clicker comprises a distal clicker part 101, a proximal clicker part 102 and a spring 103.

Figure 4:
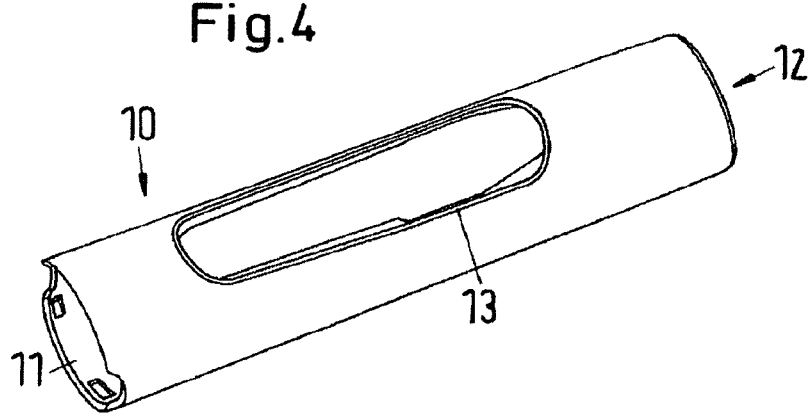
FIG. 4 shows the outer body of the drug delivery device of FIG. 1.

The outer housing part 10, which is shown in FIG. 4, is a generally tubular element having a distal part 11 for attaching the inner body 20 and a proximal part, which is provided with a rotational hard stop 12 on its inner surface (not shown) which contact mating faces of the display member 60 when the maximum units (in this example 80U) stop is engaged. The end face also serves as the end of dose dispense stop for the button 70, and the bore in the end face centers the display member 60 during both dialing and dispense. An aperture 13 is provided for receiving window insert 130. The outer body 10 provides the user with a surface to grip and react against during dispense.

Figure 20A:
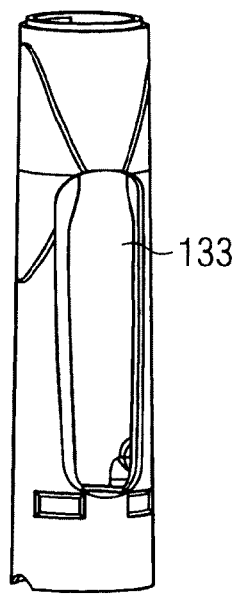
FIG. 20a shows a plastic element of the outer housing part.
Figure 20B:
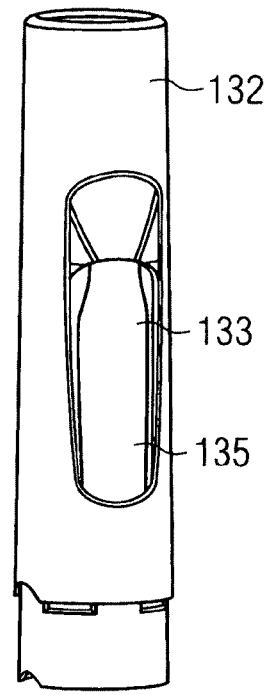
FIG. 20b shows the plastic element and a metal element of the outer housing part during assembling.
Figure 20C:
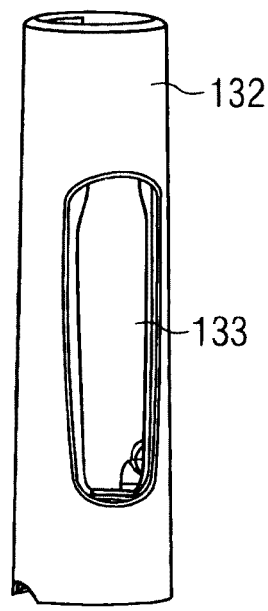
FIG. 20c shows the plastic element and the metal element of the outer housing part in an assembled state.

The outer housing part 10 comprises a metal element 132 and a plastic element 133. These elements are shown for example in FIGS. 20*a* to 20*c*. FIG. 20*a* shows the plastic element 133 of the outer housing part 10. The plastic element 133 is produced by mold flowing or injection molding. The plastic element 133 may be made of Polyoxymethylen (POM) or of another plastic material. FIG. 20*b* shows the plastic element 133 and the metal element 132 of the outer housing part 10 during assembling. In particular, the metal element 132 is slid over the plastic element 133. For example, the metal element 132 comprises a stop face (not shown), wherein the metal element 132 can be slid over the plastic element 133 until the stop face of the metal element 132 abuts the plastic element 133. The stop face of the metal element 132 may be produced by beading one end of the metal element 132. In particular, the beaded end forms the stop face of the metal element 132. The metal element 132 is produced by deep drawing. The metal element 132 may be made of aluminium or of another metal material.

The plastic element 133 is coupled to the inner housing 20. The inner housing 20 comprises snap features 139. The snap features 139 interact with the plastic element 133, thereby fixing the plastic element with respect to the inner housing 20.

The metal element 132 comprises an aperture 135, which is configured for receiving the window insert 130.

The outer surface of the plastic element 133 is adapted to the inner surface of the metal element 132. Thereby, the plastic element 133 and the metal element 132 may be accurately fitted together. Each of the plastic element 133 and the metal element 132 may have the form of a sleeve.

The plastic element 133 and the metal element 132 are fixedly coupled. In particular, the plastic element 133 and the metal element 132 are fixed together in an axial and rotational direction.

FIGS. 22*a* and 22*b* show snap features 139 of the inner housing 20. By means of the snap features 139, the outer housing part 10 is coupled to the inner housing 20. In particular, the snap features 139 are engaged with the plastic element 133 of the outer housing part 10.

FIG. 23*a* shows the metal element 132 of the outer housing part 10. The metal element 132 comprises a radial lug 138. The lug feature 138 may comprise one extended lug or a series of smaller lugs. The radial lug 138 is folded into the aperture 135. The radial lug 138 may be folded along a full perimeter of the aperture 135 or locally as shown. By means of the radial lug 138, the metal element 132 is secured to the plastic element 133, as shown in FIG. 23*b*. In particular, the radial lug 138 engages with the plastic element 133. Thereby an axial and rotational position of the metal element 132 with respect to the plastic element 133 is maintained.

In the design shown in FIG. 23*a*, the radial lug 138 is folded into the aperture 135 to a greater depth at one end of the metal element 132, but is not folded into the aperture 135 at the other end. By the radial lug 138 being folded into the aperture 135 to a greater depth at one end of the metal element 135 so that the edge folded down conforms to a plain undrafted diameter, assembling the metal element to the plastic element is made easier as the proximal end of the plastic element just has to assemble past this plain undrafted diameter. Due to the radial lug feature 138 being not present at the other end, a tab 142 (see FIG. 23*b*) of the window insert 130 may be inserted through the aperture 135 under the outer housing part 10. Thereby, the window insert 130 may be secured to the assembly.

The plastic element 133 is configured to support an underside of the window insert 130. In particular, the window insert 130 lies on the plastic element 133. Thereby, a risk of scratching a printed lower surface of the window insert 130 is minimized.

As it is intricate in practice to achieve a lug feature folded down to different depths around the aperture 135 in the metal element 132, a further embodiment as shown in FIGS. 24*a* and 24*b* omits the lug feature completely, and the metal element 132 just has a plain aperture cut into the metal element 132.

In this instance any rotational forces applied to the metal element 132 are transferred via the window insert 130 to the plastic element 133.

The metal element 132 and the plastic element 133 may be secured with respect to each other by the window insert 130, which is inserted through the aperture 135, as shown in FIG. 24b. In particular, as shown in FIG. 24a, the metal element 132 may be produced without any lug feature. By the window insert 130 extending through the aperture 135, the metal element 132 and the plastic element 133 may be axially and rotationally fixed with respect to each other.

The embodiment according to FIGS. 24a and 24b has the advantage that it is simpler to manufacture without the folded lug feature 138.

Additionally or alternatively, the plastic element 133 and the metal element 132 may be coupled to each other by press fitting. Additionally or alternatively, one or both of the plastic element 133 and the metal element 132 may comprise a feature which may fix the elements together by snap fitting. Additionally or alternatively, the plastic element 133 and the metal element 132 may be fix together by bonding with an adhesive or via application of heat to activate a bonding agent or to fuse the parts together.

Additionally or alternatively, the plastic element 133 may comprise a protrusion (not shown). The protrusion may be located at an axial end of the plastic element 133. The protrusion may extend in a radial outward direction. The metal element 132 may extend over the plastic element 133 until it abuts the protrusion. Thereby, an axial position of the metal element 132 with respect to the plastic element 133 may be defined. Furthermore, the protrusion of the plastic element 133 may comprise a nose which extends in a longitudinal direction. The nose may be configured to engage with a corresponding recess of the metal element 132. Thereby, a rotational position of the metal element 132 with respect to the plastic element 132 may be defined. There may be a plurality of nose features to improve the rotational engagement. Additionally or alternatively the metal element may have a flange at the proximal end which partially encloses the plastic element so as to restrain it axially, see FIGS. 25a and 25b.

The plastic element 133 and the metal element 132 form a functional unit. The plastic element 133 and the metal element 132 may be releasably or permanently coupled to each other.

The cap 120 comprises, as does the outer housing part 10, a metal element 150 and a plastic element 131. The metal element 150 and the plastic element 131 of the cap are shown in FIGS. 21a to 21c. In particular, FIG. 21a shows a plastic element 131 of the cap 120. FIG. 21b shows the metal element 150 attached to the plastic element 131 of the cap 120. The metal element 150 and the plastic element 131 of the cap 120 are similar to the metal element 132 and the plastic element 133 of the outer housing part 10. Therefore, it is referred to the description above.

Yet, the plastic element 131 and the metal element 150 of the cap 120 have a slightly different shape than the corresponding elements of the outer housing part 10. In particular, the metal element 150 has an end face 137, which is inclined to a longitudinal axis of the assembly. The end face 137 may be inclined to a longitudinal axis of the cap for about 60° to 80°. The end face 137 is inclined for design reasons. Furthermore, the cap 120 comprises a clip element 134. The clip element 134 is inserted into an aperture 135 of the cap 120. The clip element 134 is fixed to the cap 120 for example by snap fitting. The clip element 134 being attached to the cap 120 is shown in FIG. 21c. The clip element 134 may be configured to hold the metal element 130 and the plastic element 131 in a fixed position with respect to each other.

Figure 17:
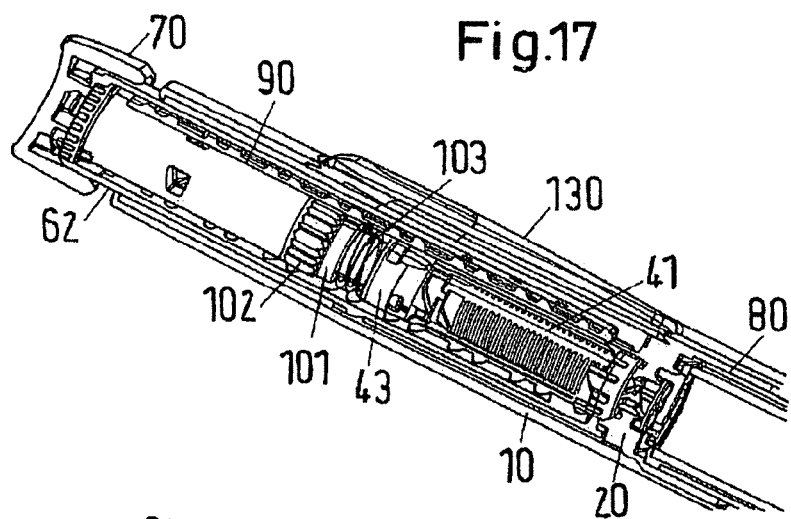
FIG. 17 shows a cut-away view of the proximal part of the drug delivery device of FIG. 1 in a zero unit position with the button released.
Figure 18:
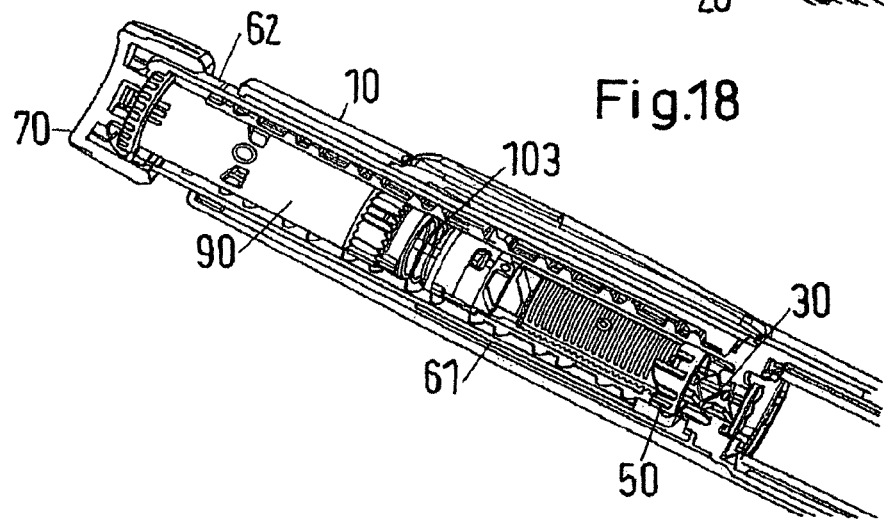
FIG. 18 shows a cut-away view of the proximal part of the drug delivery device of FIG. 1 in a position with some units dialed.
Figure 19:
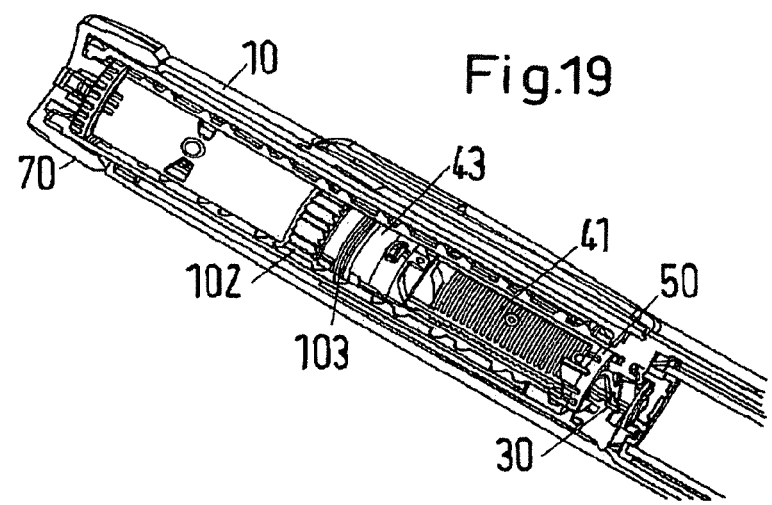
FIG. 19 shows a cut-away view of the proximal part of the drug delivery device of FIG. 1 in a zero unit position with the button pressed.

The inner body 20 is a generally tubular element having different diameter regions. As can be seen in FIGS. 17 to 19, the inner body 20 is received in the outer body 10 and permanently fixed therein to prevent any relative movement of the inner body 20 with respect to the outer body 10. The inner body has the functions to house the drive mechanism within, guiding the clickers and the last dose nut 50 via internal splines, to provide an internal thread through which the piston rod 30 (lead screw) is driven, to support and guide the number sleeve 61 and the dial sleeve 62 on an external thread form, to secure the cartridge holder 80 and to secure the outer body 10 and the window insert 130.

The outermost diameter of the inner body 20 also forms part of the visual design and remains visible when the cap 120 is secured to the cartridge holder 80 as a ring separating the cap 120 from the outer body 10. This visible ring also has depressions which align with the cap snap features on the cartridge holder 80 to indicate that the cartridge holder has been correctly fitted.

Figure 5A:
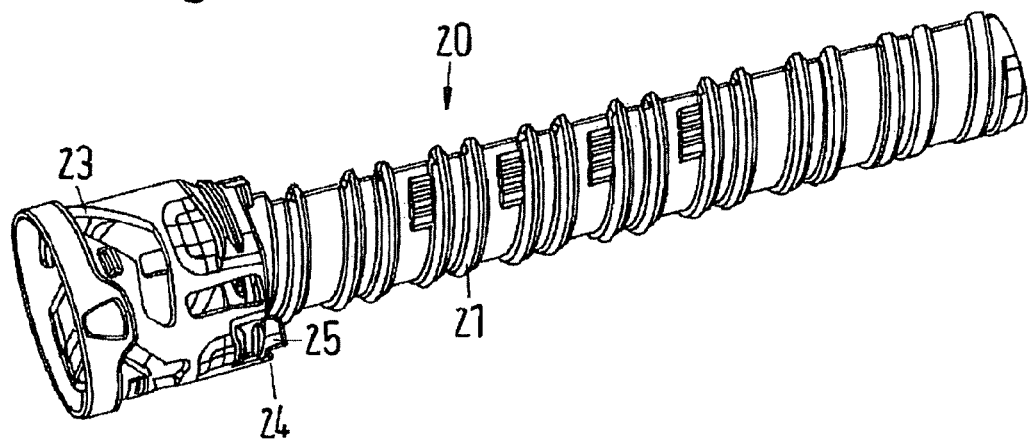
FIG. 5a shows the inner body of the drug delivery device of FIG. 1.
Figure 5B:
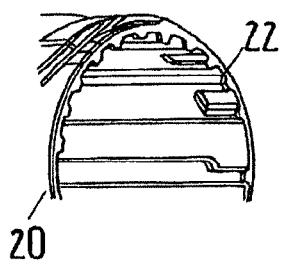

An external thread 21 is provided on the outer surface of the inner body 20. Further, splines 22 (FIG. 5b) are provided on the inner surface of the inner body 20. These internal splines 22 guide the clicker 100 axially during both dialing and dispense and also prevent the last dose nut 50 from rotating. Some of the splines may be wider to ensure correct rotational assembly of the internal components, and these wider splines may have a stepped entry and angled surface to encourage the last dose nut 50 to rotate up against the stop face on the distal drive sleeve 41 during assembly. At the open end shown in FIG. 5b there are an additional short splines which together with the alternating long splines 22 are used to rotationally lock the button 70 (dose dial grip) at the end of dispense and serve to increase the strength of the 0 U dial stop when the button 70 is depressed. This is achieved by engagement with male spline features on the clutch component 90.

Bayonet features 23 guide the cartridge holder 80 into the mechanism during cartridge replacement, compressing the cartridge bias spring 110, and then back off the cartridge holder 80 a small distance in order to reduce axial play in the mechanism. Snap features inside the inner body 20 lock the cartridge holder 80 rotationally when it has been correctly fitted. The profile of these snaps aims to prevent the user from partially fitting the cartridge holder 80, the cartridge bias spring 110 ejecting the cartridge holder 80 if the snaps have not at least started to engage. A window retention nose 24 retains the window insert 130 when the outer body 10 and window insert 130 assembly is axially inserted onto the inner body 20. Two diametrically opposite stop faces 25 define the rotational end position for the number sleeve 61. This end position is the end of dose detent position for the minimum dose (0 U).

The piston rod 30 is an elongate element having two external threads 32, 33 with opposite hand which overlap each other. One of these threads 32 engages the inner thread of the inner body 20. A disk-like bearing 31 is provided at the distal end of the piston rod 30. The bearing 31 may be a separate component as shown in FIG. 3 or may be attached to the piston rod 30 as a one-piece component via a predetermined breaking point.

The piston rod 30 transfers the dispense load from the driver 40 to the bearing 31, creating a mechanical advantage greater than 1:1 by converting the torque generated on the piston rod 30 by the driver 40 thread interface into additional axial load as the piston rod passes through the thread in the inner body 20. The piston rod 30 is reset by pressing on the bearing 31 and this in turn rotates the piston rod back into the inner body 20. This disengages and then rotates the distal drive sleeve 41, resetting the last dose nut 50 back to its starting position on the distal drive sleeve 41.

The driver 40 is a generally tubular element having in the embodiment shown in the Figures three components which are depicted in FIGS. 9 to 11 in more detail.

The distal drive sleeve 41 engages with the piston rod thread 33 to drive the piston rod 30 through the inner body 20 during dose delivery. The distal drive sleeve 41 is also permanently connected to the coupler 43 which in turn is releasably engaged through reset clutch features to the proximal drive sleeve 42. The two halves of the drive sleeve are rotationally and axially connected during dialing and dispense, but are de-coupled rotationally during device reset so that they can rotate relative to each other.

The external thread 44 engages with the last dose nut 50. The thread form has three stages, a shallow first stage (left hand side in FIG. 9) over which the nut 50 travels to count the majority of the units dialed, a fast stage over which the last dose nut moves rapidly axially prior to engaging the stop faces, and a final shallow section which ensures that when the stop faces have engaged, the axial restraint on the nut 50 extends over a reasonable length of thread form. Four equi-spaced stop faces 45 engage with mating stop faces 51 on the last dose nut 50 to limit the number of units that can be dialed. Splines 46 are provided at the proximal end of distal drive sleeve 41 to transfer torque from or to the coupler 43, which may be snapped on the distal drive sleeve 41.

The proximal drive sleeve 42 shown in FIG. 10 supports the clicker components 100 and the clutch 90 and transfers rotational movement from the dose button 90 to the coupler 42 and distal drive sleeve 41.

Teeth features 47 located at the distal end of proximal drive sleeve 42 engage with the reset clutch features on the coupler 43 to connect both halves of the drive sleeve during dialing and dispense. During reset these teeth 47 disengage.

Several splines are provided on the outer surface of proximal drive sleeve 42 engaging with distal clicker part 101, preventing relative rotation during dialing and dispense. Further splines, which are located in the middle region of proximal drive sleeve 42, engage with the clutch 90 component. They may be arranged to be non-rotationally symmetric so that the various clicker components cannot be assembled accidentally upside down.

The proximal portion of proximal drive sleeve 42 has four arms or fingers 48. A hook-like bearing surface 49 exists on the underside (as seen in FIG. 10) of flange segments on the end of the flexible fingers 48. The flexible fingers 48 are separated with gaps or slots that make space for the button 70 to snap to the clutch 90 and also enable these fingers to flex inwards during assembly of the proximal drive sleeve 42 to the dial sleeve 62. After assembly the hooks 49 retain the proximal drive sleeve 42 relative to the dial sleeve 62 under the reaction force from the spring 103. During dispense the button 70 depresses the spring 103 via the clutch 90 and the clicker components and this spring 103 is reacted through the coupler 43 to the proximal drive sleeve 42 which then through these bearing surfaces applies axial load to the dial sleeve 62. This axial load drives the dial sleeve 62 and hence number sleeve 61 along the helical thread of the inner body 20, back into the body of the device, until the 0 U stop faces on the number sleeve 61 contact the inner body 20.

The coupler 43 shown in FIG. 11 rotationally couples the two halves of the drive sleeve together during dialing and dispense, whilst allowing them to de-couple during reset. The coupler 43 has to also transfer the last dose protection stop load from the proximal drive sleeve 42 to the distal drive sleeve 41. Two sets of teeth are provided in the coupler 43 for engaging teeth 46 and teeth 47, respectively. The coupler 43 is snapped onto distal drive sleeve 41 allowing limited relative axial movement with respect to the proximal drive sleeve 42.

The nut 50 is provided between the inner body 20 and the distal drive sleeve 41 of driver 40. Stop faces 51 are located on the proximal face of last dose nut 50 to limit the number of units that can be dialed if the stop faces 51 contact stops 45 of distal drive sleeve 41. The function of the last dose nut 50 is to prevent the user from dialing beyond a finite amount. This limit is based on the dispensable volume of the cartridge 81 and when reached, the user must replace the cartridge 81 and reset the device.

External ribs 52 of the nut 50 engage splines 22 of inner body 20. An internal thread 53 of the nut engages the external thread 44 of distal drive sleeve 41. As an alternative, splines and ribs could be provided on the interface between the nut 50 and the driver 40 and threads could be provided on the interface between the nut 50 and the inner body 20. As a further alternative, the nut 50 may be designed as e.g. a half nut.

The display member 60 is a generally tubular element which is composed of number sleeve 61 and dial sleeve 62 which are snapped together during assembly to axially and rotationally constrain these two components, which thus act as a single part.

The main functions of the number sleeve 61 depicted in FIG. 8 are to provide a surface onto which dose numbers can be printed to display the dialed dose, to guide the helical path of the internal mechanism during dialing to follow the helical thread form on the piston rod 30 when threaded to the inner body 20 and to attach to the dial sleeve 62.

The number sleeve 61 is designed to be fully enclosed in the outer body 10 during dialing and dispense and therefore only the dialed dose is visible to the user through the window aperture. The number sleeve has a 0 U (minimum dose) stop face 63 to limit its travel when dialed in but the 80 U (maximum dose) stop faces that limit the dialed out condition are located on the dial sleeve 62. At the end of each dispense stroke, this stop face 63 engages with mating surface 25 on the inner body 20 to limit the rotational position of the number sleeve 61.

FIGS. 25*a* and 25*b* each show a cross section of the metal element 132 and the plastic element 133 of the outer housing part 10 showing a stop feature 140. The stop feature 140 may be an '80 Units stop' feature. In particular, the stop feature 140 may be a rotational stop. The stop feature 140 is arranged on the plastic element.

FIG. 26 shows an embodiment wherein the stop feature 140 is comprised by the metal element 132 of the outer housing part 10. The stop feature 140 is formed as a series of lug features 141. The folded lug features 141 form a bearing surface for the dial sleeve 62. This bearing is advantageously of low friction to minimize dispense force and to avoid scratching the dial sleeve 62.

The advantage of the embodiment shown in FIG. 26 is that the plastic element is much shorter and is therefore easier and cheaper to mold. In particular, the length of the plastic element 133 is about one third of the length of the metal element.

Furthermore an '80 Units torque' is transferred via the inner housing 20 to the plastic element 133 if the user counteracts this torque by holding the cartridge holder.

FIG. 27 shows an assembly with the dial sleeve 62 and the number sleeve 61 and a part of the metal element 132 comprising the stop feature 140, in particular the '80 Units stop' feature. The main surface of the metal element 132 is cut away for clarity reasons. The assembly is shown in a state where an '80 Units stop' feature on the dial sleeve 62 is engaged with the stop feature 140 of the metal element. By means of the stop feature 140, a rotational stop is provided for the dial sleeve 62.

A helical drive face 64 forms a thread that guides the number sleeve 61 during dialing and dispense to follow the helical path 21 on the inner body.

The dial sleeve 62 is assembled to the number sleeve 61 such that once assembled, no relative movement is allowed. The parts are made as separate components to enable both molding and assembly. Also, whereas the number sleeve 61 is preferably white to give contrast for the e.g. black dose numbers, the dial sleeve 62 color can be chosen to suit the aesthetics or perhaps to distinguish the drug type.

At the dose proximal end, the dial sleeve 62 has internal clutch features 65 that engage with the clutch component 90 during dialing and disengage from the clutch during dispense. These clutch features 65 rotationally lock the dial sleeve 62 to the clutch 90 during dialing and when the 0 U and 80 U stops are engaged. When the button 70 is depressed these clutch features disengage to allow the clutch 90 and drive mechanism to move axially whilst the dial sleeve 62 and number sleeve 61 spin back to the 0 U start position.

The dial sleeve 62 rotates out during dialing through its engagement with the clutch 90 and number sleeve 61, and rotates back in during dispense under the axial force applied by the proximal drive sleeve 42 to a flange-like bearing face 66 on the end of the dial sleeve. This bearing face 66 engages with the flexible arms 48 of the proximal drive sleeve 42 during dispense. Two diametrically opposite faces 67 engage with the outer body 10 when the maximum dose (e.g. 80 U) has been dialed, forming the maximum dose stop faces.

A ratchet arm 68 engages with ratchet features on the button 70 (dose dial grip) to provide audible feedback during dispense, giving one click per unit delivered. Further, this prevents the user from gripping and rotating the number sleeve 61 outwards from a partially dialed out position whilst holding the button 70 pressed in. This would back wind the piston rod 30 which would result in an under dose on the subsequent dialed dose. It may further strengthen the 0 U stop.

The button 70 which is shown in FIG. 16 serves as a dose dial grip and is retained by the clutch 90 to transfer the actions of the user to the clutch. It also carries ratchet teeth 71 that engage the ratchet arm 68 on the dial sleeve 62, which serves as the dispensing clicker giving audible feedback (ratchet clicks), and an end face 72 which serves as the dose completion stop face with the outer body 10. This end face 72 thus serves to define the end position during dispense when it contacts the outer body 10 to provide a very positive stop improving dose accuracy.

A central sleeve-like portion of button 70 is provided with four arms 73 having hook-like snap features 74 at their respective distal ends. The arms 73 form splined surfaces engaging with the clutch 90 to transfer torque from the button 70 through the clutch to the dial sleeve 62 and proximal drive sleeve 42. The snap features 74 engage apertures in the clutch 90 and are designed with angled undercut faces to maintain engagement when an axial load is applied to pull the button 70 out of the pen body 10. The space between arms 73 defines pockets giving clearance for the flexible arms 48 of proximal drive sleeve 42 to slide freely relative to the button 70 and clutch 90 when the button 70 is depressed and released during dose dispense.

Figure 6:
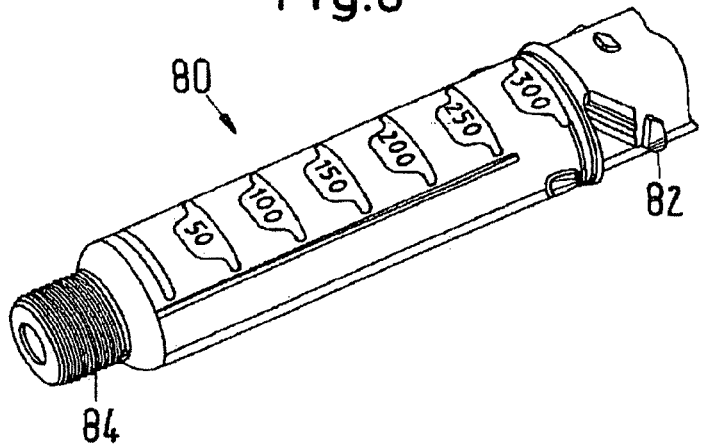
FIG. 6 shows the cartridge holder of the drug delivery device of FIG. 1.
Figure 7A:
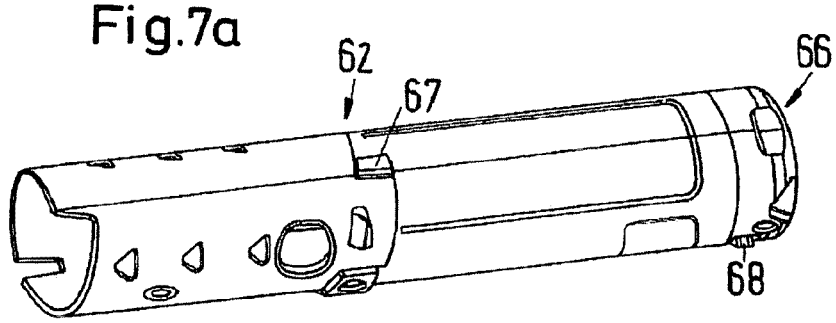
FIG. 7a shows a first display member component of the drug delivery device of FIG. 1.
Figure 7B:
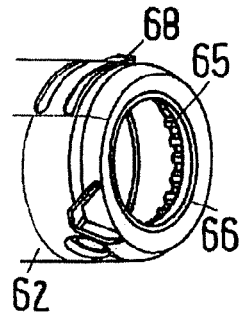

The cartridge holder 80 attaches to the inner body 20 with a bayonet connection 82 and houses the glass ampoule or cartridge 81 containing the medication to be dispensed. The cartridge holder 80 includes an aperture 83 in the rear face (as seen in FIG. 6) which if gripped by the user prevents the ampoule from falling out when the cartridge holder is removed from the inner body 20. The front face is printed with a dose number scale. The threaded distal end 84 is used to attach disposable pen needles.

A tubular clutch 90 is provided between the display member 60 and the button 70. The clutch is fixed relative to and retains the button 70 and together they travel axially relative to the proximal drive sleeve 42 when the button 70 is depressed during dispense, disengaging the clutch teeth from the dial sleeve 62. It also transfers torque from the button to the proximal drive sleeve 42, and the dialing and 0 U/80 U stop loads from the button via the clutch teeth to the dial sleeve and number sleeve.

Drive sleeve splines 91 provided on an inner surface of the clutch engage with the proximal drive sleeve 42. At the distal end face, clutch biasing teeth 92 are provided which mate with similar teeth on the proximal clicker part 102 to ensure that in the button out position (dialed dose) the clutch is locked in rotation to the proximal clicker part 102 under the biasing action of the clutch spring 103. The teeth 92 are shallow in height to prevent the proximal clicker part 102 from engaging with splines on the proximal drive sleeve 42 during dialing. Four snap apertures 93 serve to retain the snap features 74 of button 70. Near its proximal end, the clutch has splines 94 which at the end of dispense with the button 70 depressed lock to the inner body 20 to prevent the user from rotating the button 70 below the 0 U position.

Clutch teeth 95 engage with clutch teeth 65 of the dial sleeve to rotationally couple the button 70 via the clutch to the number sleeve 61. During dispense the clutch is moved axially so as to disengage these clutch teeth 95 releasing the dial sleeve 62 to rotate back into the device whilst the clutch 90 and hence driver 40 move axially to dispense the dose.

The clicker 100 comprises a distal clicker part 101, a proximal clicker part 102 and a spring 103. The clutch spring 103 serves to bias the button 70 out so that at the end of a dose the button 70 pops out, re-engaging the clutch 90 with the dial sleeve 62 ready for dialing. Further, it provides the spring force for the clicker components to act as clickers and also as detent positions for the number sleeve 61. In addition, it holds the two halves of the drive sleeves 41, 42 in rotational engagement during dialing and dispense, whilst allowing them to disengage during device reset.

The distal clicker part 101 is permanently splined to the proximal drive sleeve 42 and engages with the proximal clicker part 102 which in turn is splined to the inner body 20. During dialing when the drive sleeve is rotated relative to the inner body, the two clickers 101, 102, rotate relative to each other under the compression force of the clutch spring 103. This force combined with the clicker teeth formed on the end face of each clicker provides the clicks and also the detent dialing positions.

During dispense the two clickers 101, 102 are pressed together under the dispense load and therefore prevent relative rotation between the proximal drive sleeve 42 and inner body 20, driving the piston rod forwards to deliver the dose. The splines 104 on the inner bore rotationally couple the distal clicker part 101 to the proximal drive sleeve 42 at all times, but allow free axial movement when the button 70 is depressed during dispense and when the two clickers ride over each other during dialing. The profile of the clicker teeth 105, 106 on both distal clicker part 101 and proximal clicker part 102 are identical and ride over each other under the compressive load from the spring 103 during dialing.

The proximal clicker part 102 is permanently splined to the inner body 20 by external splines 107 which prevent relative rotation with the inner body during both dialing and dispense, providing clicks during dialing and locking the proximal drive sleeve 42 in rotation during dispense. Additional cylindrically shaped splines 108 also couple the proximal clicker part 102 rotationally to the proximal drive sleeve 42 when the button 70 is depressed, this preventing the user from dialing past 80 units with the button depressed. Proximal clicker part 102, in addition to the primary clicker teeth 106, has clutch biasing teeth 109 on the opposite end face. These teeth mate with similar teeth 92 on the clutch to ensure that in the button out position (dialed dose) the clutch is locked in rotation to the proximal clicker part 102 under the biasing action of clutch spring 103.

The cartridge bias spring 110 is assembled as two components one after the other, the lower first and the upper second. The spring combination serves to apply an end load to the cartridge 81 at extremes of tolerance so as to bias it forwards onto the end face of the ferrule in the cartridge holder 80. This ensures that when the user removes and attaches a needle, the friction between the needle cannula and septum of the cartridge does not move the cartridge 81 axially relative to the cartridge holder 80. The bias spring 110 also acts to provide a force against which the user has to connect the cartridge holder 80 and this may add to the tactile feedback of this bayonet joint. The spring 100 also serves to eject the cartridge holder 80 if the cartridge holder is not rotated into a secure position, highlighting this error to the user.

The cap 120 serves to protect the cartridge holder 80 from damage and the cartridge 81 itself from dust dirt ingress on to the area around the septum. The cap is designed to accommodate a standard pen injector needle.

The window insert 130 may include a lens to magnify the dose numbers e.g. by approximately 25% from their printed size. The window insert 130 may be back printed to protect the printed surface from abrasion and also to maximize the light entering through the window aperture, giving uniform illumination of the dose numbers and white area around these numbers. Arrows may be printed adjacent to the window aperture that indicate the dose dialed.

In the following, the function of the drug delivery device and its components will be explained in more detail with reference to FIGS. 17 to 19.

To use the device, a user has to select a dose. In the start (at rest) condition as shown in FIG. 17 the display member 60 indicates the number of doses dialed to the user. The number of dialed units can be viewed through the dose window 130 in the outer body 10. Due to the threaded engagement between the display member 60 and the inner body 20 rotation of the button 70 in a clockwise fashion causes the display member 60 to wind out of the device and incrementally count the number of units to be delivered. FIG. 18 shows an intermediate stage of dialing (e.g. 7 of 80 units).

During dose setting button 70, driver 40 and display member 60 are rotationally locked together via clutch 90. Further, button 70, driver 40 and display member 60 are axially coupled. Thus, these three components wind out of the outer housing 10 during dose setting. Clockwise rotation of the button 70 causes the driver 40 to rotate and in doing so it advances along the piston rod 30 which remains fixed throughout dialing. The clicker arrangement 100 provides tactile and audible feedback to the user when dialing doses. At the maximum settable dose of 80 units, the stop features 12 and 67 engage to prevent further dialing.

The last dose nut 50 provides the function of counting the number of dispensed units. The nut 50 locks the device at the end of cartridge life and as such no more drug can be dialed by the user. The last dose nut 50 and the driver 40 are connected via a threaded interface as explained above. Further, the last dose nut 50 is assembled into splines 22 such that the nut 50 and the inner body 20 are rotationally locked together (at all times). Rotation of the driver 40 during dialing causes the nut 50 to advance along the thread 44. The nut 50 is free to slide axially within the inner body 20 at all times which allows advancement of the nut. The change in pitch of thread 44 shown in FIG. 9 towards the final doses axially accelerates the advancement of the nut 50 towards the end of cartridge life lockout condition. At the end of life condition, the stop features 51 of the last dose nut 50 contact the corresponding features 45 on the driver 40. The splined contact with inner body 20 reacts any torque transmitted by these stop features 45.

With the desired dose dialed, the device 1 is ready for dose dispensing. This basically requires pushing button 70 which will result in a disengagement of the clutch 90 from dial sleeve 62 thus allowing relative rotation between the display member 60 and the button 70. In all conditions the driver 40 and the button 70 are rotationally locked together by engagement of arms 73 and fingers 48 and by splines 91 engaging corresponding splines on proximal drive sleeve 42. Thus, with the clutch 90 disengaged (button 70 pushed in) button 70 and driver 40 are rotationally locked together with the button 70, the driver 40 and the display member 60 still being axially coupled.

When dispensing a dose, the dose button 70 and clutch 90 are moved axially relative to the mechanism compressing the clutch spring 103. Because the proximal clicker part 102 is splined to the inner body 20 and the axial load passing through the clicker teeth 105, 106 locks the distal clicker part 101 in rotation to the proximal clicker part 102, the mechanism is forced to move axially whilst the dial sleeve 62 and number sleeve 61 are free to spin back into the outer housing 10. The interaction of mating threads between the piston rod 30, driver 40 and inner body 20 delivers a mechanical advantage of 2:1. In other words, axially advancing driver 40 causes the piston rod 30 to rotate which due to the threaded engagement of piston rod 30 with the inner body 20 advances the piston rod. During dose dispensing dispense clicker 68, 71 is active which involves button 70 and display member 60. The dispense clicker provides primarily audible feedback to the user that drug is being dispensed.

The end of this step is shown in FIG. 19. At this point the dose is complete and when the user removes the force from the end of the dose button 70, the clutch spring 103 pushes this dose button 70 rearwards, re-engaging the teeth 65 and 95 between the clutch and the dial sleeve.

Resetting the device starts with removal of the cartridge holder 80 and replacing an empty cartridge with a full cartridge 81. As the cartridge holder is re-attached, the bung of the new cartridge contacts bearing 31, thus pushing piston rod 30 back into the housing. Initially, the piston rod 30 screws into the inner body 20, thereby axially disengaging the coupler 43 from the proximal drive sleeve 42 against the biasing force of spring 103. Once disengaged the coupler 43 is free to start rotating together with distal drive sleeve 41 and continues to do so as the cartridge holder 80 is moved axially into engagement with the inner body 20. Thus, the distal drive sleeve 41 rotates with respect to the proximal drive sleeve 42 which is still rotationally constrained in inner body 20 as clicker parts 101 and 102 are pressed together by compressed spring 103. As the distal drive sleeve 41 rotates, last dose nut 50 is reset to its (distal) start position. Coupling the cartridge holder 80 to inner body 20 backs off the mechanism due to the bayonet structure 23 allowing re-engagement of the proximal drive sleeve 42 with coupler 43 and thus the distal drive sleeve 41.

LIST OF REFERENCES 1 drug delivery device
10 outer housing part
11 distal part
12 rotational hard stop
13 aperture
20 inner housing
21 external thread
22 splines
23 bayonet features
24 window retention nose
25 first rotational stop
30 piston rod
31 bearing
32 first outer thread
33 second outer thread
40 driver
41 distal driver part
42 proximal driver part component
43 coupler
44 external thread
45 stop faces
46 splines
47 teeth features
48 fingers
49 bearing surface
50 dose nut
51 stop faces
52 external ribs
53 internal thread
60 display member
61 number sleeve
62 dial sleeve
63 stop face
64 helical drive face
65 clutch features/teeth
66 bearing face
67 opposite faces
68 ratchet arm
70 button
71 ratchet teeth
72 end face
73 arms
74 snap features
80 cartridge holder
81 cartridge
82 bayonet connection
83 aperture
84 distal end
90 clutch
91 drive sleeve splines
92 clutch biasing teeth
93 snap features
94 splines
95 clutch teeth
100 clicker
101 distal clicker part
102 proximal clicker part
103 spring
104 splines
105, 106 clicker teeth
107 external splines
108 shaped splines
109 clutch biasing teeth
110 spring
120 cap
130 window
131 plastic element of cap
132 metal element of outer housing part
133 plastic element of outer housing part
134 clip element
135 aperture of cap
136 aperture of outer housing part
137 end face (of cap)
138 radial lug
139 snap feature
140 stop feature
141 lug feature stop feature
142 tab
150 metal element of cap

The invention claimed is:

1. An assembly for a drug delivery device, comprising:
a metal element and a plastic element which together form a functional unit;
an aperture comprising a distal end proximal to a distal end of the metal element, and a proximal end distal to a proximal end of the metal element;
a window component received in the aperture; and
a display member, wherein the window component is arranged such that dose related information provided on the display member can be viewed through the window component,
wherein the metal element and the plastic element are fixedly coupled to each other by the window component such that longitudinal movement and rotational movement of the metal element, the plastic element, and the window component relative to one another is prevented during use, and wherein the metal element provides an outer surface of the assembly which is configured to be handled by a user.

2. The assembly according to claim 1, wherein an outer surface of the plastic element is continuously in contact with an inner surface of the metal element.

3. The assembly according to claim 1, wherein the metal element and the plastic element have a sleeve shape.

4. The assembly according to claim 1, wherein the metal element is deep drawn.

5. The assembly according to claim 1, wherein the metal element comprises aluminum.

6. The assembly according to claim 1, wherein the metal element has a wall thickness of 0.3 mm to 0.6 mm.

7. The assembly according to claim 1, wherein the plastic element is produced by mold flowing.

8. The assembly according to claim 1, wherein the assembly is a housing for the drug delivery device.

9. The assembly according to claim 1, wherein the metal element and the plastic element are held together by press fitting or bonding.

10. The assembly according to claim 1, wherein the metal element and the plastic element are held together by a radial lug of the metal element being engaged with the plastic element.

11. The assembly according to claim 1, wherein the plastic element and/or the metal element comprise one or more stop features that are configured to prevent a user from setting a dose greater than a pre-determined maximum dose.

12. The assembly according to claim 1, wherein one of the metal element or the plastic element defines the aperture, and the other of the metal element or the plastic element defines another aperture, wherein the window component is attached to the assembly through the aperture or the other aperture.

13. The assembly according to claim 1, wherein the metal element defines the aperture, and the plastic element comprises a transparent material.

14. A drug delivery device comprising an assembly comprising:
- a metal element and a plastic element which together form a functional unit;
- an aperture comprising a distal end proximal to a distal end of the metal element, and a proximal end distal to a proximal end of the metal element;
- a window component received in the aperture; and
- a display member, wherein the window component is arranged such that dose related information provided on the display member can be viewed through the window component,
- wherein the metal element and the plastic element are fixedly coupled to each other by the window component such that longitudinal movement and rotational movement of the metal element, the plastic element, and the window component relative to one another is prevented during use, and
- wherein the metal element provides an outer surface of the assembly which is configured to be handled by a user, and the drug delivery device has a weight less than 30 grams.

15. A method of producing an assembly for a drug delivery device comprising a metal element and a plastic element which together form a functional unit, the method comprising:
- fixedly coupling the metal element and the plastic element to each other by a window component received in an aperture of the assembly such that longitudinal movement and rotational movement of the metal element, the plastic element, and the window component relative to one another is prevented during use, and such that the metal element provides an outer surface of the assembly which is configured to be handled by a user, the window component being arranged such that dose related information provided on a display member can be viewed through the window component, wherein the aperture comprises a distal end proximal to a distal end of the metal element, and a proximal end distal to a proximal end of the metal element; and
- sliding the metal element over the plastic element in a longitudinal direction.

16. The assembly according to claim 1, wherein the assembly comprises a cap for a drug delivery device.

17. The assembly of claim 10, wherein the radial lug extends through the aperture to hold together the plastic element and the metal element.

18. The assembly of claim 17, wherein the radial lug extends along an entirety of a perimeter of the aperture.

19. The assembly of claim 17, wherein the radial lug extends only along a portion of the perimeter of the aperture.

20. The assembly of claim 1, wherein an inner perimeter of the metal element defines an entire length of a perimeter of the aperture.

* * * * *

UNITED STATES PATENT AND TRADEMARK OFFICE
CERTIFICATE OF CORRECTION

PATENT NO.         : 10,668,218 B2
APPLICATION NO.    : 14/914472
DATED              : June 2, 2020
INVENTOR(S)        : David Aubrey Plumptre Page 1 of 1

It is certified that error appears in the above-identified patent and that said Letters Patent is hereby corrected as shown below:

On the Title Page

In Column 1 Item (73) (Assignee), Line 2, delete "Frankfut" and insert -- Frankfurt --

Signed and Sealed this
Twenty-fifth Day of August, 2020

Andrei Iancu
*Director of the United States Patent and Trademark Office*